(12) United States Patent
Elmeguenni

(10) Patent No.: US 10,195,630 B2
(45) Date of Patent: Feb. 5, 2019

(54) BOTTLE AND METHOD FOR MANUFACTURING A DIP TUBE FOR A BOTTLE

(71) Applicant: ALBEA LE TREPORT, Le Treport (FR)

(72) Inventor: Mohamed Elmeguenni, Friville Escarbotin (FR)

(73) Assignee: ALBEA LE TREPORT, Le Treport (FR)

( * ) Notice: Subject to any disclaimer, the term of this patent is extended or adjusted under 35 U.S.C. 154(b) by 14 days.

(21) Appl. No.: 15/293,418

(22) Filed: Oct. 14, 2016

(65) Prior Publication Data

US 2017/0106390 A1    Apr. 20, 2017

(30) Foreign Application Priority Data

Oct. 15, 2015 (FR) .................................. 15 59829

(51) Int. Cl.
| | |
|---|---|
| *B05B 15/00* | (2018.01) |
| *B05B 15/30* | (2018.01) |
| *B05B 11/00* | (2006.01) |
| *A61K 8/34* | (2006.01) |
| *A61Q 13/00* | (2006.01) |
| *A45D 34/02* | (2006.01) |

(Continued)

(52) U.S. Cl.
CPC ................ *B05B 15/30* (2018.02); *A61K 8/34* (2013.01); *A61Q 13/00* (2013.01); *B05B 11/0037* (2013.01); *B05B 11/3001* (2013.01); *A45D 34/02* (2013.01); *A45D 2200/054* (2013.01); *A61K 2800/87* (2013.01); *B29C 49/04* (2013.01); *B29L 2031/7158* (2013.01)

(58) Field of Classification Search
CPC ............... B05B 15/005; B05B 11/0037; B05B 11/3001; A61Q 13/00; A61K 8/34; A61K 2800/87; B29C 49/04; B29L 2031/7158; A45D 34/02; A45D 2200/054
USPC .................................. 222/321.1–321.9, 464.1
See application file for complete search history.

(56) References Cited

U.S. PATENT DOCUMENTS

| | | | | |
|---|---|---|---|---|
| 4,964,532 A | * | 10/1990 | Kirschner | ............ B67D 1/0078 222/1 |
| 5,495,965 A | * | 3/1996 | Knickerbocker | ..... B05B 15/005 222/382 |
| 2003/0075264 A1 | | 4/2003 | Terakado et al. | |

(Continued)

FOREIGN PATENT DOCUMENTS

FR    2837799 A1    10/2003

OTHER PUBLICATIONS

Jun. 23, 2016 (FR)—International Search Report—Appl. 1559829.

*Primary Examiner* — Donnell Long
(74) *Attorney, Agent, or Firm* — Banner & Witcoff, Ltd.

(57) ABSTRACT

A bottle containing a solution, said bottle has a transparent or at least translucent body which is surmounted by a ring (3) provided with an opening to which a dispensing member (4) for the solution is joined. The dispensing member has a dispensing member body (6) and a dip tube (7) which communicate with one another, the tube being immersed in the solution (1) in order to allow the dispensing member to be supplied with solution to be dispensed. The dip tube has a silicone such that the difference between the refractive index of the tube and the refractive index of the solution is less than or equal to 0.04.

18 Claims, 3 Drawing Sheets

(51) Int. Cl.
   *B29L 31/00*     (2006.01)
   *B29C 49/04*     (2006.01)

(56) References Cited

U.S. PATENT DOCUMENTS

| | | | |
|---|---|---|---|
| 2005/0133540 A1* | 6/2005 | Hornsby | B05B 1/3436 |
| | | | 222/333 |
| 2006/0073294 A1* | 4/2006 | Hutchinson | B29C 44/04 |
| | | | 428/35.7 |
| 2007/0125804 A1 | 6/2007 | Thomson et al. | |
| 2009/0166383 A1* | 7/2009 | Canfield | A45D 34/04 |
| | | | 222/207 |
| 2012/0050994 A1* | 3/2012 | Boday | H01L 23/473 |
| | | | 361/702 |
| 2014/0175122 A1* | 6/2014 | Crawford | B05B 11/0037 |
| | | | 222/78 |
| 2014/0197248 A1 | 7/2014 | Govers | |
| 2016/0060002 A1* | 3/2016 | Karotko | B65D 25/48 |
| | | | 222/464.5 |
| 2016/0346515 A1* | 12/2016 | Buller | A61M 25/01 |
| 2017/0021976 A1* | 1/2017 | Wang | B29C 49/22 |

* cited by examiner

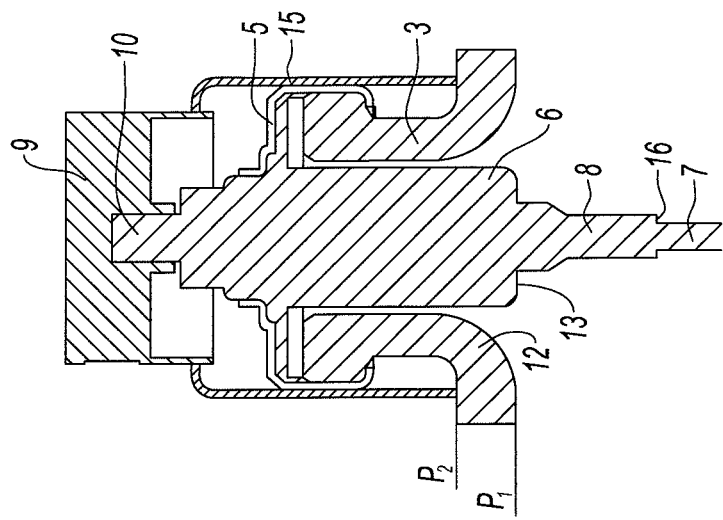
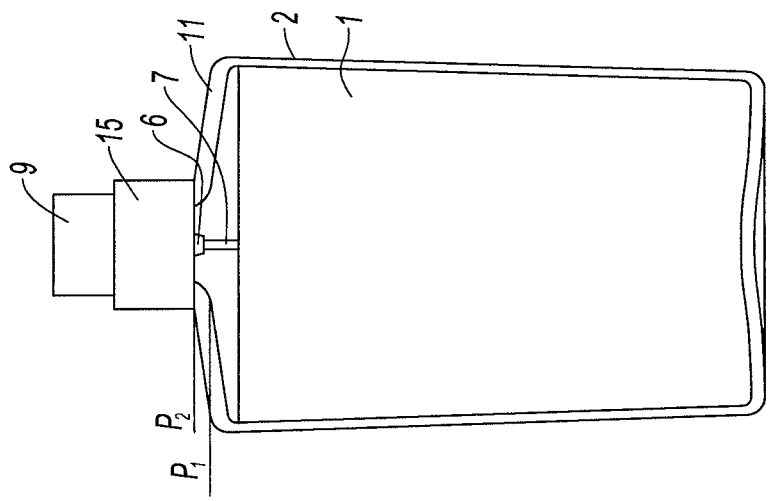
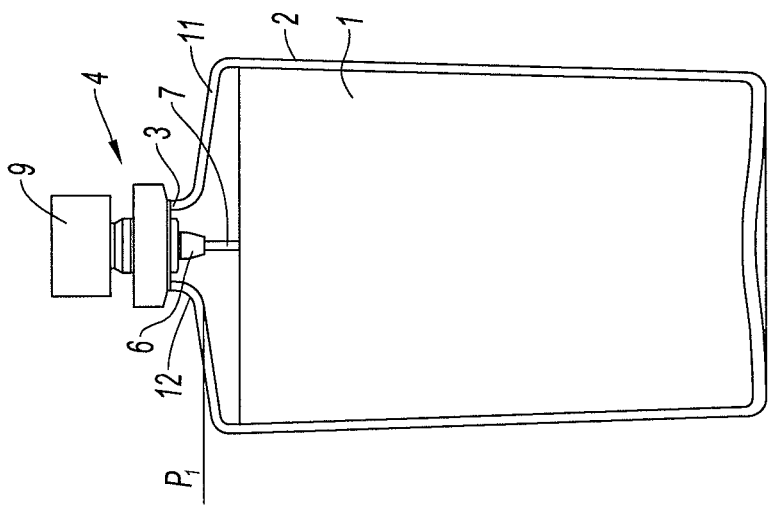

BOTTLE AND METHOD FOR MANUFACTURING A DIP TUBE FOR A BOTTLE

CROSS-REFERENCE

This application claims priority to French application serial No. 1559829 filed Oct. 15, 2015 which application is hereby incorporated by reference in its entirety.

FIELD

The invention relates to the field of bottles containing a solution, in particular bottles comprising a transparent or at least translucent body and a dip tube immersed in the solution in order to allow a dispensing member, for example a pump, to be supplied with solution.

BACKGROUND

The dip tube is conventionally made of a polymeric material which is colourless, transparent and can easily be extruded in the form of tubes of small dimensions. Furthermore, the materials used for said tube have to exhibit mechanical properties suitable to allow them to be joined to the pump body at high speeds, and have to exhibit sufficient resilience to resume a substantially straight configuration after having been wound around a storage reel. For example, the materials used according to the prior art are made of polyolefin, of the polypropylene or polymethylpentene (TPX) type.

For aesthetic reasons, perfumers want the dip tube to be invisible, because otherwise it would mar the appearance of the bottles.

In order to make these tubes invisible in the solution, for perfume products, it is known to make them from a fluoropolymer-based material having a refractive index close to that of the solution. It is also necessary for the method for transforming them to provide a crystallinity of less than 13%. These fluoropolymers are not only costly and not readily available (one single supplier of these materials worldwide), but also present a health risk. The fluorine migrates into the liquid and becomes inhalable when sprayed by a dispensing system, and therefore comes into contact with the mucosa of the respiratory system. Tubes made of fluoropolymers are difficult to handle owing to their electrostatic effect which attracts dust, other particles and their packaging film. These tubes also have a mechanical performance which is poorer than that of fluorine-free polyolefin tubes. They retain the curves or bends from the assembly processes or from transport.

There is therefore a need for a bottle which comprises a dip tube which has features which contribute to making the dip tube invisible in a solution and which does not have the drawbacks mentioned above.

SUMMARY

To this end, the present invention proposes a bottle containing a solution, said bottle comprising a transparent or at least translucent body which is surmounted by a ring provided with an opening to which a dispensing member for the solution is joined, said dispensing member comprising a dispensing member body and a dip tube which communicate with one another, said tube being immersed in the solution in order to allow said dispensing member to be supplied with solution to be dispensed, said dip tube comprising a silicone such that the difference between the refractive index of said tube and the refractive index of said solution is less than or equal to 0.04.

The present invention also proposes a bottle designed to contain a solution, said bottle comprising a transparent or at least translucent body which is surmounted by a ring provided with an opening to which a dispensing member for the solution is joined, said dispensing member comprising a dispensing member body and a dip tube which communicate with one another, said tube being designed to be immersed in the solution in order to allow said dispensing member to be supplied with solution to be dispensed, said dip tube comprising a silicone such that the refractive index of said tube is between 1.36 and 1.44.

Using a material comprising a silicone having a refractive index close to that of the solution contained in the bottle makes it possible to obtain a dip tube which is substantially invisible in its part which is immersed in the solution. In particular, perfume solutions such as eau de toilettes have a refractive index of between 1.37 and 1.39. Furthermore, this material has the advantage of being able to be manufactured easily, in particular by extrusion, in tubes of small dimensions, and to exhibit sufficient resilience not to retain the memory of the curvature imposed when stored on a reel. These features are of major industrial relevance since the dip tube is introduced at high speed into the bottle via the opening, the small dimensions of which necessitate good reliability in positioning said tube relative to said opening. However, the presence of excessive curvature on the tube does not make it possible to guarantee this positioning, nor furthermore to guarantee the positioning of the lower end of the tube in the bottle as is required to dispense all of the solution contained in the bottle. Furthermore, the majority of silicones are approved for applications in the fields of pharmaceuticals and foodstuffs. They also have the advantage of having very low surface tension and of being water-repellent, anti-static and anti-soil, which improves their handling ability during manufacture of the bottle.

According to various embodiments of the invention, which may be taken together or separately:
  the refractive index of said tube is approximately 1.40,
  the refractive index of said silicone is between 1.36 and 1.44, preferably approximately 1.40,
  the difference between the refractive index of said silicone and the refractive index of said solution is less than or equal to 0.04,
  said silicone is polydimethylsiloxane (PDMS),
  the refractive index of said polydimethylsiloxane is between 1.36 and 1.44, preferably approximately 1.40,
  the difference between the refractive index of said polydimethylsiloxane and the refractive index of said solution is less than or equal to 0.04,
  said polydimethylsiloxane is pure polydimethylsiloxane or a polydimethylsiloxane alloy,
  said solution is an alcoholic solution,
  said solution is an alcoholic perfume solution,
  the transmittance of said tube is greater than 90%, preferably between 90 and 99.5%,
  the transmittance of said silicone is greater than 90%, preferably between 90 and 99.5%,
  the transmittance of said polydimethylsiloxane is greater than 90%, preferably between 90 and 99.5%,
  said dip tube comprises a core, in particular made of polyolefin,
  said silicone and/or polydimethylsiloxane is in the form of a coating on the surface of said core, said tube further comprises solid nanoparticles and/or microparticles, said tube comprises a coating provided on said core, said coating comprising all or some of said solid nanoparticles and/or microparticles, said solid nanoparticles and/or microparticles have a refractive index selected from between 1.3 and 1.5, said solid nanoparticles and/or microparticles are silica and/or glass, said tube further comprises at least one semi-crystalline or amorphous polymer, said semi-crystalline or amorphous polymer(s) is/are selected from among polymethylpentene (TPX), a cyclic olefin copolymer (COC), polymethyl polymethacrylate (PMMA) or a mixture thereof, the surface of said tube comprises a marking, said marking is a decoration, a text and/or a geometric shape, said dispensing member is a pump, said dip tube is mounted on said dispensing member body by means of a joining part, said dip tube is integral with said dispensing member body, said bottle comprises other elements made from a material comprising a silicone such that the refractive index of said element(s) is between 1.36 and 1.44.

The invention also relates to a dip tube for a bottle as defined previously.

The invention further relates to a method for manufacturing such a tube, said method comprising a step of obtaining said tube at least from silicone, in particular polydimethylsiloxane.

According to various features of the invention, which may be taken together or separately:

said method comprises a step of forming a core of the tube and a step of applying a coating to the surface of the core, said coating comprises silicone and/or polydimethylsiloxane, said application of said coating of silicone and/or polydimethylsiloxane is carried out by spraying, dipping or vacuum deposition, the polydimethylsiloxane is solid or liquid polydimethylsiloxane, the solid polydimethylsiloxane is hot-vulcanisable or cold-vulcanisable, said coating comprises solid nanoparticles and/or microparticles, said application of said coating comprising solid nanoparticles and/or microparticles is carried out by spraying.

said solid nanoparticles and/or microparticles have a refractive index selected from between 1.3 and 1.5, said solid nanoparticles and/or microparticles are silica and/or glass, said tube, in particular said core, is obtained by extrusion and/or by compression moulding, said method comprises a step of marking the surface of said dip tube, said marking is applied by laser, heat transfer, screen printing and/or pad printing, said marking is a decoration, a text and/or a geometric shape, said method comprises a step of treatment which reduces the coefficient of friction of said tube, said treatment which reduces the coefficient of friction is a surface plasma treatment, quenching, in particular on emerging from extrusion, or lubrication of the surface, said lubrication is carried out using a silicone oil, said quenching is carried out by providing a temperature gradient of between 200 and 300° C., in particular with a liquid at a temperature of from −40° C. to −60° C., on emerging from extrusion.

BRIEF DESCRIPTION OF THE DRAWINGS

Other features, aims and advantages of the invention will become apparent from the following description, which is given purely by way of illustrative and non-limiting example and should be read with reference to the accompanying drawings, in which:

FIG. 1 and FIG. 2 are side views of a bottle according to the invention, without (FIG. 1) and with (FIG. 2) a collar mounted on a ring of the bottle, respectively;

FIGS. 3 to 8 are partial views in longitudinal section showing the mounting of a pump on a bottle according to embodiments of the invention.

DETAILED DESCRIPTION OF EXEMPLARY ASPECTS

Figure 4:
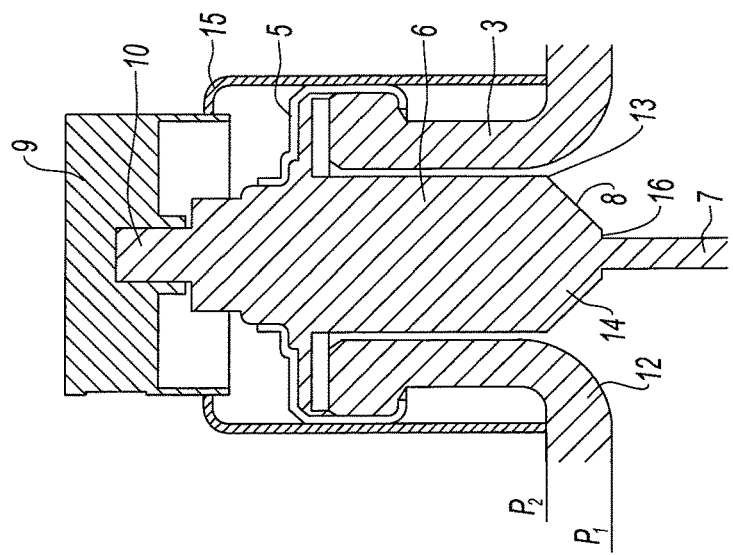

In the description, the terms of positioning in space are taken with reference to the position of the bottle depicted in FIG. 1.

In relation to the drawings, there is described below a bottle containing a solution 1, in particular a solution which is colourless or slightly coloured. This is preferably an alcoholic solution, in particular an alcoholic perfume solution.

The bottle comprises a body 2 which is transparent or at least translucent, made for example of colourless or slightly coloured glass or plastics material. The body 2 is provided to contain the solution, allowing it to be seen by the user.

The body 2 is surmounted by a ring 3 which is provided with an opening to which a dispensing member for the solution is joined. The drawings depict joining of the dispensing member 4 to the outside of the ring 3 by means of a cup 5, although the invention is not limited to this specific embodiment.

The dispensing member 4 comprises a dispensing member body 6 and a dip tube 7 which communicate with one another.

In a first illustrated embodiment, the dispensing member is a pump 4. Said dip tube 7 is mounted on the dispensing member body 6 (referred to in this embodiment as "pump body") in the lower part by means of a joining part 8. The dip tube 7 is immersed in the solution 1 to allow said pump to be supplied with solution to be dispensed.

In another embodiment not shown, said dip tube may be integral with said dispensing member body. In other words, said dip tube and the dispensing member body are made in one piece.

The pump body 6 and the joining part 8 incorporate functional members (not shown) which, by actuation of a push button 9, make it possible to dispense the solution by means of a spray nozzle 10 and a nozzle (not shown). A large number of pump arrangements and kinematics which permit dispensing in particular of a perfume on which the invention may be implemented are known.

As shown in the drawings, the dip tube 7 according to the invention is substantially invisible in its part which is immersed in the solution.

In order to achieve this, the dip tube 7 comprises a silicone such that the difference between the refractive index of said tube 7 and the refractive index of said solution 1 is less than or equal to 0.04. Thus, said tube comprises a silicone such that the refractive index of said tube 7 is between 1.36 and 1.44, preferably approximately 1.40, when the refractive index of the solution 1 contained in the bottle is between 1.37 and 1.39. In other words, the refractive index of said tube 7 has to be close to the refractive index of the solution 1 contained in the bottle.

The transmittance (or transparency) of said tube 7 is thus greater than 90%, preferably between 90 and 99.5%.

Consequently, a silicone having a refractive index of between 1.36 and 1.44, preferably approximately 1.40, will be selected. Advantageously, the silicone is polydimethylsiloxane (PDMS) having a refractive index of approximately 1.40. Polydimethylsiloxane also has the advantage of being approved for use in pharmaceuticals and foodstuffs Polydimethylsiloxane also has the advantage of having very low surface tension and of being water-repellent, anti-static and anti-soil. Polydimethylsiloxane is also rubber-like and consequently has very good shape memory and hyperelastic mechanical behaviour. These particular features permit better handling ability of said tube 7 during manufacture of the bottle, in particular during its insertion into the joining part, and also facilitate its manufacture and storage.

Said polydimethylsiloxane may be pure polydimethylsiloxane or a polydimethylsiloxane alloy. It may be solid or liquid polydimethylsiloxane. In the case of solid polydimethylsiloxane, it is advantageously hot-vulcanisable or cold-vulcanisable.

Advantageously, said tube 7 is obtained by extrusion and/or by compression moulding.

In one embodiment, said tube further comprises solid nanoparticles and/or microparticles. Said solid nanoparticles and/or microparticles preferably have a refractive index selected from between 1.3 and 1.5 in order not to modify the refractive index of the tube 7 and so that the tube remains substantially invisible in its part which is immersed in the solution. Said solid nanoparticles and/or microparticles are in particular silica and/or glass.

Said tube may also comprise a coating comprising solid nanoparticles and/or microparticles. These are the solid nanoparticles and/or microparticles described previously. In this case, the method for manufacturing the dip tube 7 comprises a step of applying a coating comprising the solid nanoparticles and/or microparticles. Said application is carried out for example by spraying.

The use of solid nanoparticles and/or microparticles makes it possible to improve the mechanical behaviour of the dip tube 7, in particular to make it more rigid and thus to facilitate its insertion into the joining part 8.

Likewise, in order to improve the mechanical behaviour of the dip tube 7, said tube may furthermore comprise at least one semi-crystalline or amorphous polymer. This may be selected from among polymethylpentene (TPX), a cyclic olefin copolymer (COC), polymethyl polymethacrylate (PMMA) or a mixture thereof.

Another solution for improving the mechanical behaviour of the dip tube 7 is to carry out an additional step of quenching on emerging from extrusion. Said quenching is carried out by providing a temperature gradient of between 200 and 300° C. with a liquid at a temperature of from −40° C. to −60° C.

In one specific embodiment, said dip tube 7 comprises a polyolefin core and said silicone and/or polydimethylsiloxane is in the form of a coating on the surface of said core.

The method for manufacturing the dip tube 7 then comprises a step of applying a coating of silicone and/or polydimethylsiloxane to the surface of said core. Preferably, said coating of silicone and/or polydimethylsiloxane is applied by spraying, dipping or vacuum deposition of polydimethylsiloxane. Using a polyolefin tube makes it possible to improve the mechanical behaviour of the dip tube 7 while retaining the properties of the polydimethylsiloxane, that is to say to be substantially invisible when immersed in the solution 1 contained in the bottle.

In an additional step of the manufacturing method, said tube 7 may also undergo treatment which reduces the coefficient of friction. Such treatment makes it possible, in particular, to reduce the coefficient of friction and facilitate insertion of the tube 7 into the joining part 8. The treatment may be a surface plasma treatment, quenching on emerging from extrusion or lubrication of the surface. Lubrication is carried out for example using a silicone oil.

In a variant not shown, the dip tube 7 may comprise a marking. In this case, the manufacturing method may comprise a marking step. This may for example be laser engraving, printing on a zone of the periphery of said tube, heat transfer, screen printing and/or pad printing. In embodiments, the marking may be in the form of a decoration, a text, or a geometric shape. The combination of the invisible nature of the dip tube 7 and the presence of the marking then gives the visual impression that said marking is floating in the solution 1.

In order to improve the overall invisibility of the pump 4, the invention also provides for the pump body 6 to be able to be produced from a transparent or at least translucent material. Likewise, when the pump 4 comprises functional members which are potentially visible in the body 2 of the bottle, in particular when said members are arranged close to or in the joining part 8, the invention provides for said members to be made of transparent or at least translucent material.

According to one embodiment, the pump 4 comprises an inlet valve for the solution which is provided in the joining part 8, said valve comprising a ball made of transparent or at least translucent material. In the event that the pump 4 comprises a spring in its lower part, it is also envisaged to make this spring from transparent or at least translucent material. Furthermore, the spring may be positioned in a hidden zone entirely included within the ring 3 of the bottle.

The invention further provides for the different elements of the bottle, in particular those made from a transparent or at least translucent material which are described above, to be made from a material comprising a silicone such that the refractive index of said element(s) is between 1.36 and 1.44, that is to say the material described previously and used to manufacture the dip tube 7, and in all cases a material of the same type.

The bottle comprises an upper wall 11 on which the ring 3 is formed by means of a fillet 12, the lower end of which is contained in a substantially transverse plane P1. This plane P1 is in particular defined by the intersection between the generatrix of the upper wall 11 and the generatrix of the opening in the ring 3.

In order to limit the visibility of the pump body 6 in the body 2 of the bottle, the lower end 13 of the pump body 6 is located substantially in or above the transverse plane P1. "Lower end" 13 of the pump body 6 is understood to mean the zone which is adjacent to the joining part 8.

In FIGS. 3 to 5 and 8, the body 6 has an upper cylindrical part and a joining part 8 having two successive diameters. In these embodiments, the lower end 13 is the zone comprising the rim for connection to the joining part 8.

Figure 6:
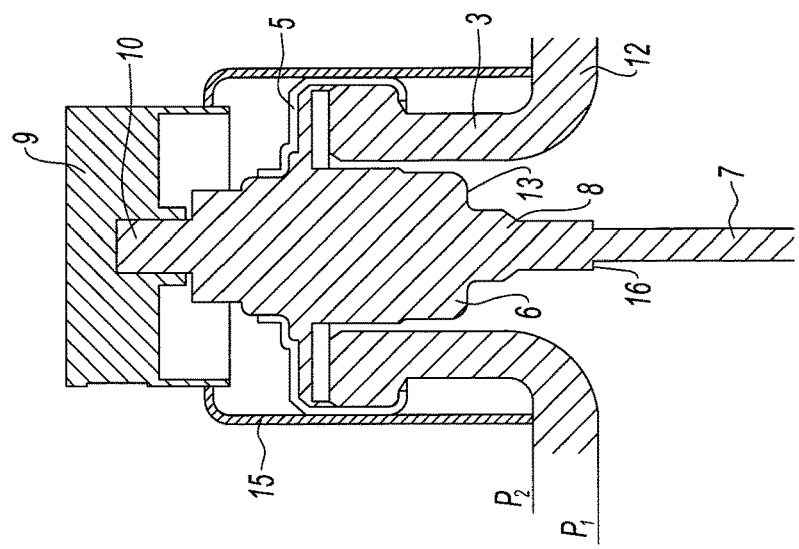
Figure 7:
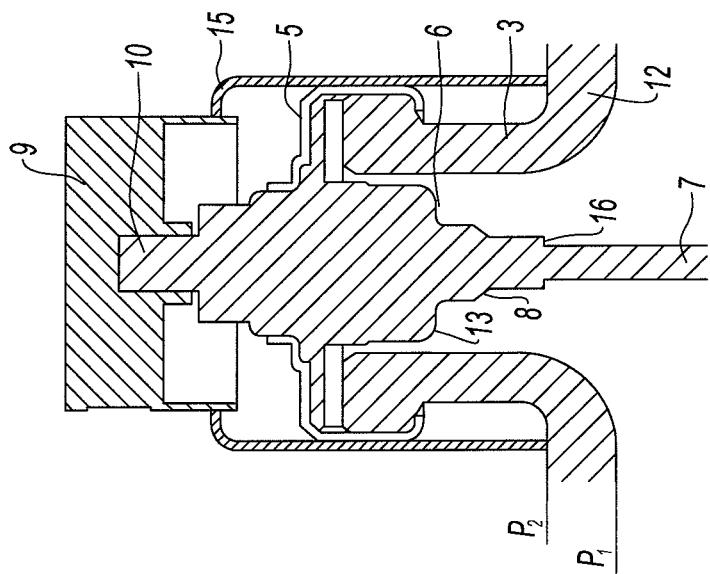

In FIGS. 6 and 7, the body 6 has an upper cylindrical part and the joining part 8 has a bevelled external profile 14 which extends from the lower end 13 of said body. In these embodiments, the joining part 8 may be of small dimensions and the presence of the bevelled profile 14 makes it possible to give an optical effect which limits the visibility of the lower end of the pump 4.

In FIG. 2, the bottle further comprises a collar 15 which is mounted around the ring 3, the lower end of said collar resting on the upper face of the wall 11 in a substantially transverse plane P2. The collar 15 thus makes it possible to mask the zone joining the pump 4 to the ring 3.

In FIG. 3, the lower end 13 of the body 6 is located substantially in the plane P1. In FIGS. 4 and 6, the lower end 16 of the joining part 8, that is to say the zone starting from which the dip tube 7 is visible, is located substantially in the plane P1.

Figure 5:
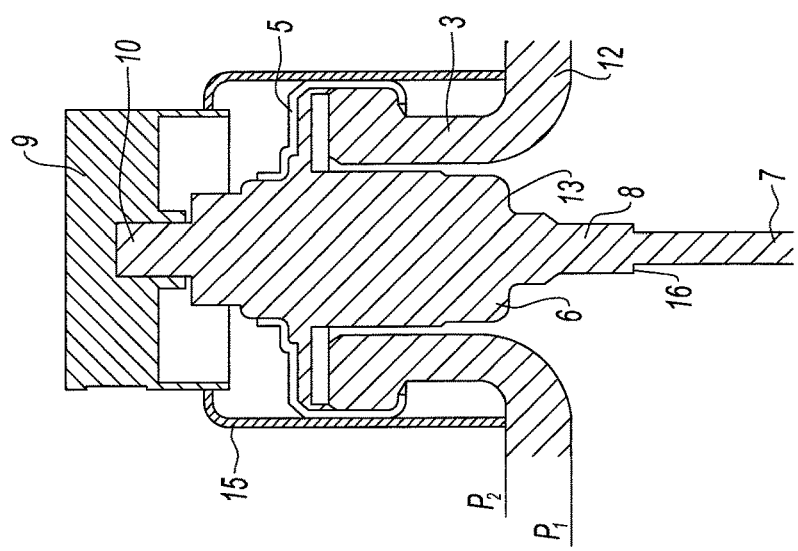
Figure 8:
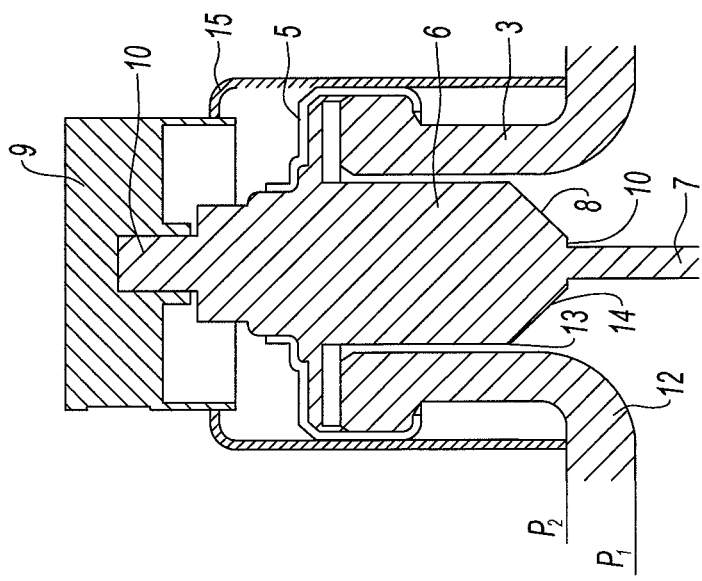

In FIG. 5, the lower end 13 of the body 6 is located substantially in the plane P2. In FIGS. 7 and 8, the lower end 16 of the joining part 8 is located substantially in the plane P2.

The invention claimed is:

1. Manufacturing method for manufacturing a dip tube for a bottle containing a solution, said bottle comprising a transparent or at least translucent body which is surmounted by a ring provided with an opening to which a dispensing member for the solution is joined, said dispensing member comprising a dispensing member body and said dip tube which communicate with one another, said dip tube being immersed in the solution in order to allow said dispensing member to be supplied with solution to be dispensed, said dip tube comprising a silicone such that the difference between the refractive index of said dip tube and the refractive index of said solution is less than or equal to 0.04, said method comprising a step of obtaining said dip tube starting at least from silicone, said dip tube being obtained by extrusion and/or by compression moulding, said method further comprising a step of quenching said extruded tube, said quenching step being carried out by providing a temperature gradient of between 200 and 300° C. with a liquid at a temperature of from −40° C. to −60° C., on emerging from extrusion.

2. Manufacturing method according to claim 1, wherein said tube is obtained at least from solid or liquid polydimethylsiloxane.

3. Manufacturing method according to claim 2, wherein the solid polydimethylsiloxane is hot-vulcanisable or cold-vulcanisable.

4. Manufacturing method according to claim 1, comprising a step of treatment which reduces the coefficient of friction of said tube.

5. Bottle containing a solution, said bottle comprising a transparent or at least translucent body which is surmounted by a ring provided with an opening to which a dispensing member for the solution is joined, said dispensing member comprising a dispensing member body and a dip tube which communicate with one another, said tube being immersed in the solution in order to allow said dispensing member to be supplied with solution to be dispensed, said dip tube comprising a silicone such that the difference between the refractive index of said tube and the refractive index of said solution is less than or equal to 0.04, said dip tube being manufactured by the method according to claim 1.

6. Bottle according to claim 5, wherein said dip tube comprises a polyolefin core and said silicone is in the form of a coating on the surface of said core.

7. Bottle according to claim 5, wherein said silicone is polydimethylsiloxane (PDMS).

8. Bottle according to claim 5, wherein said tube further comprises solid nanoparticles and/or microparticles.

9. Bottle according to claim 8, wherein said solid nanoparticles and/or microparticles have a refractive index selected from between 1.3 and 1.5.

10. Bottle according to claim 5, wherein said tube further comprises at least one semi-crystalline or amorphous polymer.

11. Bottle according to claim 10, wherein said semi-crystalline or amorphous polymer(s) is/are selected from among polymethylpentene (TPX), a cyclic olefin copolymer (COC), polymethyl polymethacrylate (PMMA) or a mixture thereof.

12. Bottle according to claim 5, wherein said solution is an alcoholic perfume solution.

13. Bottle according to claim 5, wherein said dispensing member is a pump.

14. Bottle according to claim 5, wherein said dip tube is mounted on said dispensing member body by means of a joining part.

15. Bottle according to claim 5, wherein said dip tube is integral with said dispensing member body.

16. Bottle according to claim 5, comprising other elements made from a material comprising a silicone such that the refractive index of said element(s) is between 1.36 and 1.44.

17. Manufacturing method for manufacturing a dip tube for a bottle designed to contain a solution, said bottle comprising a transparent or at least translucent body which is surmounted by a ring provided with an opening to which a dispensing member for the solution is joined, said dispensing member comprising a dispensing member body and said dip tube which communicate with one another, said dip tube being designed to be immersed in the solution in order to allow said dispensing member to be supplied with solution to be dispensed, said dip tube comprising a silicone such that the refractive index of said dip tube is between 1.36 and 1.44, said method comprising a step of obtaining said dip tube starting at least from silicone, said dip tube being obtained by extrusion and/or by compression moulding, said method further comprising a step of quenching said extruded tube, said quenching step being carried out by providing a temperature gradient of between 200 and 300° C. with a liquid at a temperature of from −40° C. to −60° C., on emerging from extrusion.

18. Bottle designed to contain a solution, said bottle comprising a transparent or at least translucent body which is surmounted by a ring provided with an opening to which a dispensing member for the solution is joined, said dispensing member comprising a dispensing member body and a dip tube which communicate with one another, said tube being designed to be immersed in the solution in order to allow said dispensing member to be supplied with solution to be dispensed, said dip tube comprising a silicone such that the refractive index of said tube is between 1.36 and 1.44, said dip tube being manufactured by the method according to claim 17.

* * * * *